(12) United States Patent
Freier et al.

(10) Patent No.: US 10,328,096 B2
(45) Date of Patent: Jun. 25, 2019

(54) COMPOSITION COMPRISING CHITOSAN FOR USE IN THE PREVENTION AND/OR IN THE TREATMENT OF INCONTINENCE AND/OR IMPOTENCE IN A SUBJECT UNDERGOING PROSTATECTOMY

(71) Applicants: Thomas Freier, Mainz (DE); Universita' degli Studi di Torino, Turin (IT)

(72) Inventors: Thomas Freier, Mainz (DE); Stefano Geuna, Orbassano (IT); Francesco Porpiglia, Orbassano (IT)

(73) Assignees: UNIVERSITA' DEGLI STUDI DI TORINO, Turin (IT); Thomas Freier, Mainz (DE)

( * ) Notice: Subject to any disclaimer, the term of this patent is extended or adjusted under 35 U.S.C. 154(b) by 0 days.

(21) Appl. No.: 15/641,348

(22) Filed: Jul. 5, 2017

(65) Prior Publication Data
US 2018/0008625 A1  Jan. 11, 2018

(51) Int. Cl.
| A61K 31/722 | (2006.01) |
| A61K 9/70 | (2006.01) |
| A61K 45/06 | (2006.01) |
| A61K 9/00 | (2006.01) |
| A61K 47/36 | (2006.01) |
| A61L 27/20 | (2006.01) |

(52) U.S. Cl.
CPC .......... *A61K 31/722* (2013.01); *A61K 9/0024* (2013.01); *A61K 9/7007* (2013.01); *A61K 45/06* (2013.01); *A61K 47/36* (2013.01); *A61L 27/20* (2013.01); *A61L 2430/34* (2013.01)

(58) Field of Classification Search
None
See application file for complete search history.

(56) References Cited

U.S. PATENT DOCUMENTS

| 2006/0286032 A1 | 12/2006 | Ryu et al. | |
| 2011/0311632 A1* | 12/2011 | Roorda | A61K 31/722 424/488 |
| 2014/0079686 A1* | 3/2014 | Barman | A61K 8/4953 424/94.67 |
| 2015/0216894 A1* | 8/2015 | McCarthy | A61K 47/12 514/55 |

FOREIGN PATENT DOCUMENTS

| EP | 2159259 A1 * | 3/2010 | C08L 5/08 |
| EP | 3266467 A1 | 1/2018 | |
| FR | 2848118 A1 * | 6/2004 | A61L 31/041 |

(Continued)

OTHER PUBLICATIONS

Ahmed (Hydrogel:Preparation, characterization, and Applications: A review, Journal of Advanced Research,vol. 6, Issue 2, Mar. 2015, pp. 105-121. (Year: 2015).*

(Continued)

*Primary Examiner* — Robert A Wax
*Assistant Examiner* — Melissa S Mercier
(74) *Attorney, Agent, or Firm* — Silvia Salvadori, P.C.; Silvia Salvadori (57) ABSTRACT

Composition comprising chitosan for use in the prevention and/or treatment of incontinence and/or impotence in a subject undergoing prostatectomy.

8 Claims, 5 Drawing Sheets

(56) References Cited

FOREIGN PATENT DOCUMENTS

| WO | WO-03068281 A1 * | 8/2003 | ............. A61L 15/28 |
|----|------------------|--------|--------------------------|
| WO | 2009056602 A1 | 5/2009 | |
| WO | 2016073723 A1 | 5/2016 | |

OTHER PUBLICATIONS

Nakiri et al. (Bilateral Neurovascular Bundles Sparing Prostatectomy Preserves Sexual Function with Localized Prostate Cancer, Kurume Medical Journal, 55, 63-69, 2008). (Year: 2008).*
Intention to grant EP application No. 17176184.4 dated Jun. 4, 2018.
Search Report and Written Opinion of correspondent European Application No. EP 17176184 dated Aug. 28, 2017.
Text of EP17176184.4 for grant.
"Chitosan Capsules OEM Europe", Internet Jun. 28, 2016, http://www.web.archive.org/web/20160628132141/http://www.tiens-tianshi.com/chitosan-capsules-oem-europe-htm [retrieved on Mar. 8, 2017.
Jordan O. et al., "Novel Injectable urethral bulking agents for the treatment of urinary incontinence," Journal of Materials Science: Materials in Medicine, vol. 15, No. 4, Apr. 1, 2004 pp. 519-522.
Patel Vipul R. et al., "Dehydrated human amnion/chorion membrane allograft nerve wrap around the prostatic neurovascular bundle accelerates early return to continence and potency following robot-assisted radical prostectomy: propensity score-matched analysis.", European Urology, Jun. 2015, vol. 67, No. 6, Jun. 2015, pp. 977-980.
Search Report and Written Opinion of Priority Application IT201600070911 dated Mar. 10, 2017.

* cited by examiner

COMPOSITION COMPRISING CHITOSAN FOR USE IN THE PREVENTION AND/OR IN THE TREATMENT OF INCONTINENCE AND/OR IMPOTENCE IN A SUBJECT UNDERGOING PROSTATECTOMY

This non-provisional application claims priority to and the benefit of Italian Patent Application No. 102016000070911 filed on Jul. 7, 2016 the content of which is incorporated herein by reference in its entirety.

FIELD OF THE INVENTION

This disclosure relates to a composition comprising chitosan for use in prevention and/or treatment of incontinence and/or impotence in a subject undergoing prostatectomy.

BACKGROUND OF THE INVENTION

Prostate cancer is the most common cancer among European and American men. Treatment of prostate cancer commonly involves surgical therapy including radical prostatectomy. However, despite the increasing use of nerve-sparing techniques, such as robot-assisted surgery, urinary incontinence and erectile dysfunction remain major adverse consequences of radical prostatectomy.

Cavernous nerve injury caused by different factors, including mechanical traction damage to the neurovascular bundle during mobilization of the prostate, as well as post-operative inflammation of the neurovascular bundle, is the main reason for post-surgical erectile dysfunction.

Different materials have been tested to reduce the rate of erectile dysfunction, in order to ultimately improve the quality of life for patients.

For example, sural nerve grafts have been used as interponates to replace completely resected neurovascular bundles in patients, leading, however, to rather unpredictable and unsatisfactory results (Scardino and Kim, "Rationale for and results of nerve grafting during radical prostatectomy", Urology 2001, 57, 1016).

In animal experiments, a 2 mm rat cavernous nerve gap was either bridged with a biodegradable polyester conduit optionally containing collagen sponge (Hisasue et al., Cavernous nerve reconstruction with a biodegradable conduit graft and collagen sponge in the rat", J Urol 2005, 173, 286), or with a cross-linked alginate gel sheet (Matsuura et al., Cavernous nerve regeneration by biodegradable alginate gel sponge sheet placement without sutures", Urology 2006; 68, 1366).

However, as the human neurovascular bundle is composed of a heterogeneous network of nerve fibers and blood vessels, unlike the cable-like structure in the rat, results cannot be transferred from the rat model to the clinical situation.

Modern surgery focuses on nerve-sparing techniques which results in an increased restoration of erectile function by preserving the integrity of the neurovascular bundles.

While mechanical damage to the neurovascular bundle can be minimized by the experienced surgeon, the post-surgical inflammation remains a problem, which has to be addressed.

For example, a biodegradable polyester membrane containing brain-derived neurotrophic factor and adipose-derived stem cells has been tested in a rat cavernous nerve crush injury model, and an improved erectile function was observed compared to the non-cell containing group (Piao et al., "Therapeutic effect of adipose-derived stem cells and BDNF-immobilized PLGA membrane in a rat model of cavernous nerve injury", J Sex Med 2012, 9, 1968).

The application of growth factors and anti-inflammatory substances to preserve and regenerate the prostatic neurovascular bundle has been further advanced by the use of dehydrated human amnion/chorion membranes as source of neurotrophic factors and cytokines.

In the clinical setting, at one month post-surgery, approximately 30% of the patients regained potency and urinary continence in both the treated and control groups while at three months, approximately 70% of the patients in the treated group were potent and 95% continent, with slightly lower numbers observed for the control group (Patel et al., "Dehydrated human amnion/chorion membrane allograft nerve wrap around the prostatic neurovascular bundle accelerates early return to continence and potency following robot-assisted radical prostatectomy: propensity score-matched analysis", Eur Urol 2015, 67, 977).

As both the manufacture process and the regulatory approval and commercialization of a medical device in combination with growth factors and cellular components are demanding and expensive processes, there is still a need for simple technical solutions, preferably based on biocompatible and biodegradable components, that can efficiently support the early return of continence and potency in patients following prostatectomy.

SUMMARY OF THE INVENTION

The object of the present disclosure is to provide a biocompatible and biodegradable composition, which overcomes the above reported drawbacks.

The above object is achieved thanks to the subject matter recalled specifically in the ensuing claims, which are understood as forming an integral part of this disclosure.

According to the instant disclosure, the above object is achieved by a composition comprising chitosan for use in prevention and/or treatment of incontinence and/or impotence in a subject undergoing prostatectomy, preferably radical prostatectomy.

In one or more embodiments, the composition comprising chitosan is intended for a surgical application, specifically for being applied in contact with the prostatic neurovascular bundle of the subject undergoing prostatectomy.

Moreover, herein disclosed is a method for protecting a prostatic neurovascular bundle of a subject, wherein the composition comprising chitosan, preferably in a form of a film, is applied in contact with the prostatic neurovascular bundle of the subject undergoing prostatectomy.

BRIEF DESCRIPTION OF THE DRAWINGS

One or more embodiments will now be described, purely by way of non-limiting example, with reference to the annexed drawings, wherein.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

In an embodiment, the instant description concerns a chitosan-based composition for use in preventing and/or treating impotence in a subject undergoing prostatectomy, preferably radical prostatectomy.

The Inventors of the instant application surprisingly found that a chitosan-based composition as herein disclosed is able to improve the outcome of the radical prostatectomy, specifically, achieving a faster recurrence of potency and a reduced rate of erectile dysfunction in a subject who underwent radical prostatectomy. In addition, the composition disclosed herein may allow a faster recurrence of continence and a reduced rate of incontinence.

Moreover, thanks to the biocompatibility and to the antimicrobial and haemostatic properties of chitosan, inflammation, infection and bleeding time reduction can also be achieved. The composition herein disclosed has the further advantage of reducing the risk of infections thanks to the antibacterial properties of chitosan.

In one or more embodiments, a high biocompatibility and bioactivity of the composition may be obtained by using chitosan in form of native chitosan.

In the context of the present disclosure, the expression "native chitosan" refers to the chemical structure of chitosan, i.e. a poly(N-acetyl-D-glucosamine-co-D-glucosamine) copolymer or a poly(D-glucosamine) homopolymer.

Any cross-linked or otherwise chemically modified chitosan is considered a chitosan derivative, having different properties than native chitosan. Cross-linking of chitosan, either ionically or covalently, may lead to the blockage of active functionalities of the biomaterial, namely the amine group.

In the context of the present disclosure the term "native chitosan" includes both the chitosan base and chitosan in form of a chitosan salt.

In one or more embodiments, the composition comprises chitosan, preferably chitosan base, in an amount at least 50%, more preferably at least 90%, more preferably at least 95% by weight (w/w) of the composition, based on the non-aqueous components of the composition.

In one or more embodiments, the composition may comprise chitosan either in form of a base and in form of a chitosan salt. Preferably, the composition comprises at least one chitosan salt in an amount of 50% or less, more preferably 10% or less, more preferably 5% or less by weight (w/w) related to the total weight of chitosan.

The presence of chitosan in form of a salt can allow a good adhesion of the composition to the neurovascular bundle thus avoiding a premature detachment from the site of implantation. The chitosan salt is soluble in an aqueous solvent or physiological medium of neutral pH. Thus, wet tissue can etch the chitosan film surface, providing for a durable contact with the prostatic neurovascular bundle.

In one or more embodiments, chitosan salts may be derived from the dissolution of chitosan in an aqueous solution of one or more inorganic acids, such as hydrochloric acid, and/or organic acids selected from the group consisting of monobasic or multibasic organic acids having from 2 to 12 carbon atoms and a first pKa value between 1 and 5, such as for example acetic acid, citric acid, lactic acid, malic acid, succinic acid, mandelic acid, oxalic acid, tartaric acid, ascorbic acid, etc.

In one or more embodiments, chitosan may be present in the composition in form of a chitosan base.

In one or more embodiments, the composition consists of chitosan, preferably native chitosan.

In one or more embodiments, the composition comprises chitosan with a degree of acetylation of 40% or less, preferably 20% or less, more preferably 10% or less.

In one ore more embodiments, the composition comprising chitosan herein disclosed is essentially free of toxic compounds.

In one or more embodiments, the composition comprises glycerol in addition to chitosan, preferably in an amount between 1 and 10% by weight, based on the non-aqueous components of the composition.

The composition herein disclosed is intended for a surgical application, specifically for application on the prostatic neurovascular bundle of a subject undergoing prostatectomy.

The composition according to the present disclosure may be in any convenient form for application at the surgical site, such as solution, powder, microspheres, flakes, tube, fibres, mesh, coating, or film.

In one or more embodiments, the composition herein disclosed is in form of a film, preferably a solid film or a gel-like film.

In one or more embodiments, the composition may be in form of a freeze-dried or solvent-dried bioabsorbable film.

In one or more embodiments, the composition may be present in form of a flexible film, which may be continuous or interrupted (e.g. perforated).

The time of biodegradability of the composition, for example in form of film, can be tuned by selecting the degree of acetylation (DA) of chitosan contained therein. The possibility of tuning the biodegradation time allows to avoid premature disintegration of the chitosan composition at the implantation site.

In one or more embodiments, the composition comprising chitosan herein disclosed may further comprise other components, such as for example at least one pharmaceutically active and/or bioactive constituent.

In one or more embodiments, bioactive constituents may be selected from the group consisting of proteins, peptides, nucleic acids, low molecular weight drugs, such as antibiotics or anti-inflammatory drugs, agonists or antagonists of the innate immune system, stimulating or differentiating growth factors for stimulating or differentiating growth of at least one cell sub-type, and mixtures thereof.

In one or more embodiments, the composition may further comprise biological cells, such as for example adipose-derived stem cells.

In one ore more embodiments, the composition may be applied on the prostatic neurovascular bundle of a subject by spraying or injecting a chitosan solution which may be derived from the dissolution of chitosan in an aqueous solution of one or more inorganic acids and/or organic acids.

In one or more embodiments, the composition, for example in form of a film, may be applied on the prostatic neurovascular bundle of a subject.

In one or more embodiments, the composition in form of a solid composition, preferably in form of a film can have a smooth surface, preferably with an average roughness $R_a$ of 1 μm (micrometer) or less, preferably 0.5 μm or less, more preferably 0.1 μm or less, as determined by atomic force microscopy.

Advantageously, a smooth surface can reduce the mechanical irritation at the implantation site, thereby reducing the risk of damaging the neurovascular bundle.

In one or more embodiments, the chitosan composition in form of film may present a thickness comprised between 1 and 1000 μm, preferably between 10 and 100 μm, more preferably between 20 and 50 μm.

In one or more embodiments, the surface area of the composition in form of a film may be comprised in the range between 1 and 50 cm$^2$, preferable between 5 and 25 cm$^2$, more preferably between 10 and 15 cm$^2$.

Such a surface area allows covering the prostatic neurovascular bundle completely or partially and, preferably some of the surrounding tissue.

In one or more embodiments, the composition herein disclosed, preferably in form of a film, may have a water uptake capacity of less than 100%, preferably comprised between 25% and 80% by weight, more preferably between 50% and 75%.

In one or more embodiments, the chitosan composition in form of a film may contain at least one hole (opening), which allows absorption and diffusion of physiological liquids and fast fluid exchange through the film bulk structure.

The at least one hole may have a diameter size of 1000 μm or less, more preferably 500 μm or less, more preferably 250 μm or less. In a preferred embodiment, the at least one hole may have a diameter size of 1 μm or more, preferably 10 μm or more, more preferably 100 μm or more. In one or more embodiments, the diameter size of the holes of the film is between 100 μm and 250 μm.

In one or more embodiments, the holes may cover an area of 50% or less of the film surface, more preferably 10% or less, more preferably 1% or less.

In one or more embodiments, a preferred flow rate of physiological fluids through the chitosan composition in form of a film containing holes is 0.001 ml/min/cm$^2$ or more, preferably 0.01 ml/min/cm$^2$ or more, more preferably 0.1 ml/min/cm$^2$ or more.

Thanks to this property, the accumulation of fluid underneath the composition during implantation can be reduced or prevented thus favouring its adherence to the neurovascular bundle.

In one or more embodiments, the composition is transparent. Advantageously, this can make it easier for a physician to inspect the application to the neurovascular bundle.

In one or more embodiments, the composition, once applied at the surgical site, may be sutured.

Advantageously, this property allows the fixation of the chitosan-based composition to the surgical site and prevents dislodgement from the neurovascular bundle.

In one or more embodiments, the suture retention strength based on a Prolene USP 6/0 suture and evaluated by a mechanical tester is 0.05 N or more, preferably 0.5 N or more when measured in the dry state, and 0.01 N or more, preferably 0.1 N or more when measured in the wet state.

Materials and Methods

1H NMR Spectroscopy

Chitosan used as a starting material in the examples below was obtained in form of fine flakes from Chitinor (Norway).

The degree of acetylation (DA) was determined by 1H NMR spectroscopy, as disclosed in Lavertu et al., "A validated 1H NMR method for the determination of the degree of deacetylation of chitosan", J Pharm Biomed Anal 2003, 32, 1149.

Chitosan was analyzed in a mixture of 0.25% DCl in $D_2O$ at a chitosan concentration of approximately 0.5% (w/v).

The spectra were recorded using a Bruker Avance III HD 300 spectrometer. The DA, calculated by comparing the integrated area under the peaks associated with H2-H6 of the D-glucosamine subunit with that of the methyl group, was determined as 15.9% for chitosan as purchased, and 5.5% for deacetylated chitosan obtained as disclosed in the following.

Figure 1:
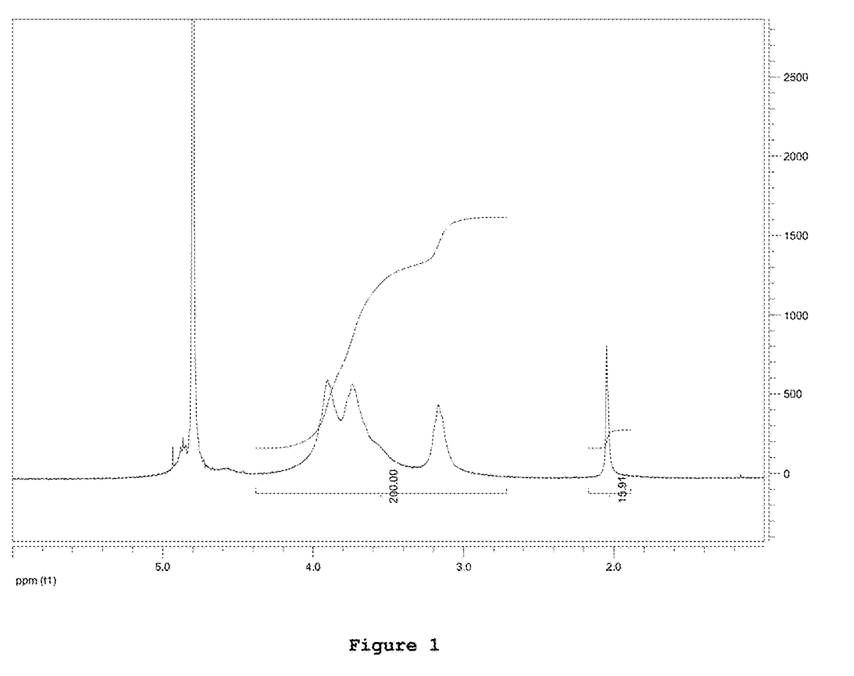
FIG. 1: 1H NMR spectrum of native chitosan as purchased.

FIG. 1 shows a 1H NMR spectrum obtained from this commercially available chitosan.

Figure 2:
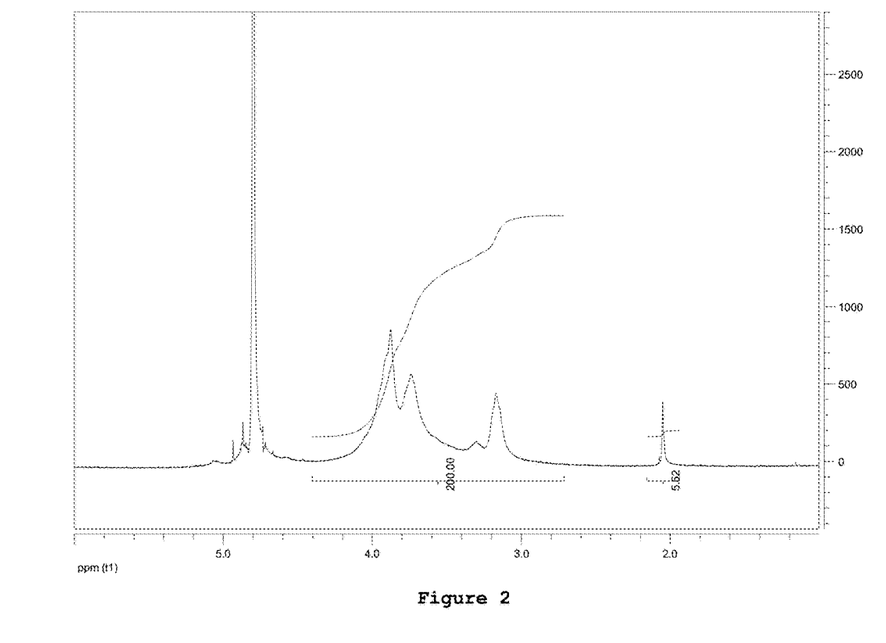
FIG. 2: 1H NMR spectrum obtained from chitosan deacetylated after a hydrolysis step applied to the commercial product.

FIG. 2 shows a corresponding 1H NMR spectrum obtained from chitosan deacetylated after a further hydrolysis step applied to the commercial product as described further below.

Deacetylation of Chitosan 50 g (grams) of chitosan flakes as obtained from the supplier Chitinor were placed in a glass container and 500 g of a 45% (w/v) aqueous sodium hydroxide solution were added.

The glass container was well shaken to mix the components, and placed in an oven for 2 hours at 80° C. It was then removed from the oven and 500 ml (milliliters) of distilled water were added.

The mixture was filtered through a 250 μm sieve. Then, chitosan was washed with distilled water until the pH of the filtrate reached approx. 6.5, and dried, resulting in chitosan having a DA of 5.5% as determined by 1H NMR spectroscopy (FIG. 2).

Preparation of a Chitosan Composition in Form of a Solid Film 7.5 g of chitosan having a degree of acetylation of 5% were dissolved in 500 ml of a 0.5% (w/v) aqueous acetic acid by gently shaking for 24 h.

144 ml of the chitosan solution was poured into a square-shaped mold, 24×24 cm$^2$ (square centimeters) in size, and left in a dust-free environment for drying at room temperature.

The dried film was placed for 2 hours in a bath containing a solution of 1.5% (w/v) ammonia in methanol/water 90/10 (v/v). The film was then removed from the bath and dried at room temperature. The resulting film has a content of approx. 100% (w/w) of chitosan, based on the non-aqueous components of the film. The remaining water content of the film is less than 10% (w/w).

A defined pattern of holes of approx. 160 μm diameter was made by gently rolling a perforator over the film. Such pattern of holes covers an area of approx. 1% of the film surface.

Figure 3:
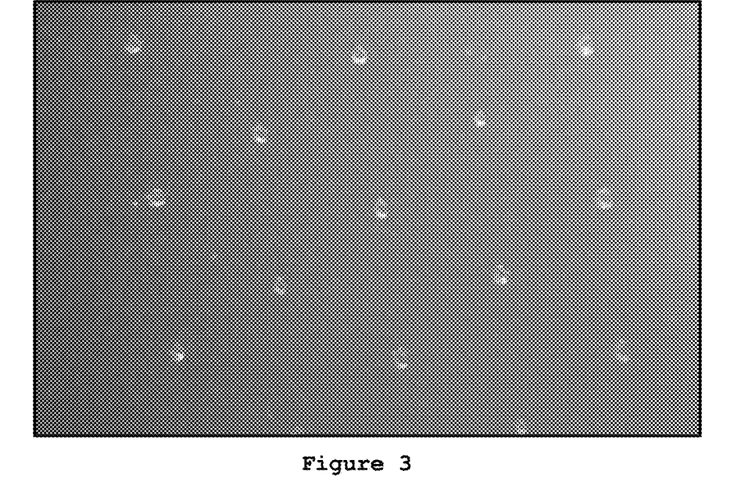
FIG. 3: Chitosan composition in form of a solid film containing holes according to one embodiment of the instant disclosure.

FIG. 3 shows the resulting perforated film. The film was then cut into 3×4 cm samples, placed in sterilization bags and sterilized using ethylene oxide.

Water Uptake of the Composition Comprising Chitosan in Form of a Solid Film

The composition comprising chitosan in form of film, produced as described above, was weighted, and then placed in distilled water for 15 min.

The weight of the obtained wet film was compared to the weight of the dry film, and the water uptake was determined to be 55% by weight.

Flow Rate Through the Composition Comprising Chitosan in Form of a Solid Film

The composition comprising chitosan in form of a film, produced as described above, was fixed to the bottom opening of a tube having a diameter of 14 mm and filled with 5 ml of phosphate buffered solution of pH 7. The flow rate for complete emptying of the tube was determined as between approx. 0.6 and 1.6 ml/min/cm$^2$.

Suture Retention Strength of the Composition in Form of a Solid Film

The composition comprising chitosan in form of a solid film, produced as described above, was fixed at the lower clamp of a mechanical tester (Thümler Z3). A Prolene USP 6/0 suture was passed through the film and attached to the upper clamp of the mechanical tester. A constant speed of 200 mm/min was applied, and the resistance to rupture of the film was determined as 1.06 N for dry and 0.17 N for wet (phosphate-buffered solution at pH 7) film samples.

Cancer Cell Proliferation Evaluation

The proliferation rate of a PC3 cell line (derived from a human adenocarcinoma) and of a glial cell line RT4-D6P2T used as control, was carried out with media collected after 15 days of chitosan film dissolution.

The PC3 cell line was purchased from ATCC (American Type Culture Collection; Manassas, Va., USA 20110-2209), and the RT4-D6P2T cell line was purchased from ATCC (American Type Culture Collection; Manassas, Va., USA 20110-2209). RT4-D6P2T are rat peripheral glial cells, derived from a schwannoma.

Conditioned medium formulations were obtained by incubating the prepared medium (Dulbecco's Modified Eagle's Medium, DMEM, for RT4-D6P2T cell line and DMEM-F12 medium for PC3 cell line) for 2 weeks at 37° C. and 5% $CO_2$ in the presence of chitosan films (4 chitosan films for 40 ml of culture medium). Afterwards this medium was used for proliferation experiments.

As control media, samples of DMEM and DMEM-F12, without chitosan films, were maintained in the same conditions (2 weeks at 37° C. and 5% $CO_2$), and then used for proliferation experiments.

Culture Medium Formulations:

DMEM (SIGMA ALDRICH) supplemented with 100 units·mL$^{-1}$ penicillin, 0.1 mg·ml$^{-1}$ streptomycin, 1 mM sodium pyruvate, 2 mM L-glutamine, 2% heat-inactivated fetal bovine serum (FBS, Invitrogen).

DMEM-F12 (SIGMA ALDRICH) supplemented with 100 units·mL$^{-1}$ penicillin, 0.1 mg·ml$^{-1}$ streptomycin, 1 mM sodium pyruvate, 2 mM L-glutamine, 2% heat-inactivated fetal bovine serum (FBS, Invitrogen).

50000 cells (25000 cells/ml) were plated and cultured in presence of conditioned media and their proliferation was evaluated after 1, 3 and 6 days.

The number of cells was assessed using a hemocytometer chamber. Each experiment was repeated in triplicate (technical triplicate), to minimize the technical error, and this was repeated in three independent experiments (biological triplicate), to give the statistical validity. Data are shown as mean±SD.

Regeneration Assay

Harvested dorsal root ganglion (DRGs) and ganglia of vagus nerve from female adult rats were maintained in Leibovitz's medium (Invitrogen, Monza, Italy) for 1 hr under sterile conditions. The connective-tissue capsules were then mechanically reduced and the explants were half-cut.

Figure 5:
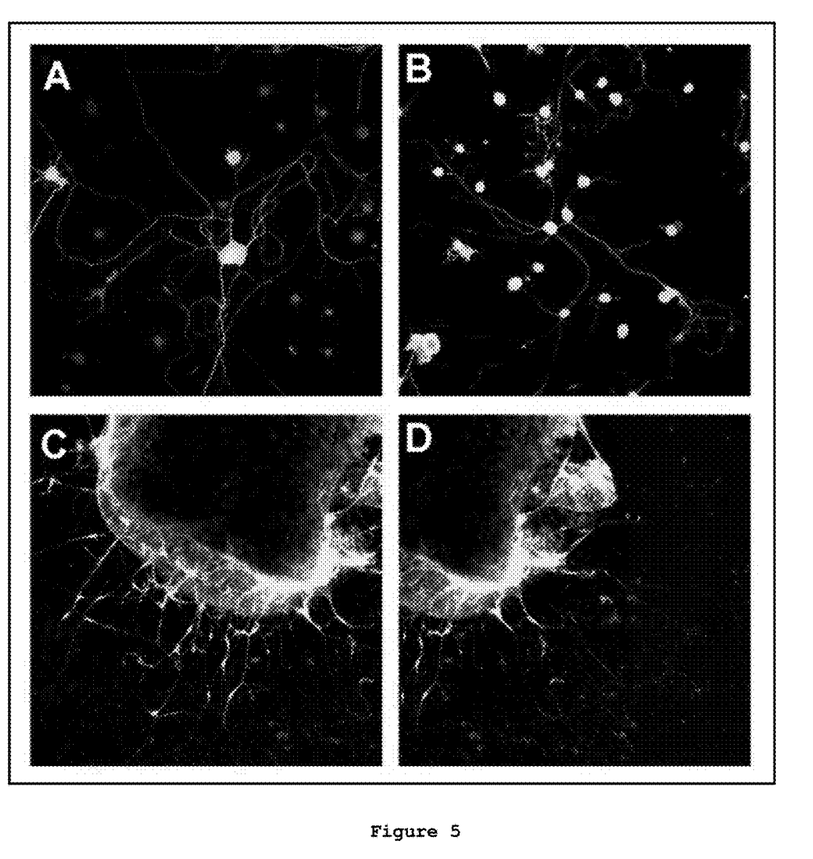
FIG. 5: Regenerative capabilities of dissociated cultures and ex vivo explants derived from somatic and autonomic ganglia grown on a chitosan film according to one embodiment of the instant disclosure.

Afterwards the dissociated sensory neurons from DRG explants (FIG. 5 A-B), and total explants from the vagus nerve ganglia (FIG. 5 C-D) were adhered onto matrigel-coated (BD Biosciences, Bedford, Mass., USA) glass coverslips and onto chitosan films, and incubated at 37° C. for 1 hr before serum-free medium (SFM) was added.

Briefly, SFM medium is composed of 50% (v/v) F12 nutrient mixture, 50% (v/v) basal medium Eagle (BME), $2×10^{-3}$ M glutamine, 0.5% (v/v) 100× PSN antibiotic mixture (all Invitrogen, Monza, Italy), 10 mg/ml bovine albumin serum, $1×10^{-4}$M putrescine, 0.1 mg/ml transferrin, $3×10^{-8}$ mg/ml selenium, 0.005 mg/ml insulin, $3.8×10^{-5}$M vitamin C, 7.5 mg/ml glucose (all Sigma, Milan, Italy) in culture-grade water. To evaluate the bioactivity (neurite outgrowth inductive potential) of the CS-substrates the explants were then maintained for three days in SFM at 37° C. with 5% $CO_2$ and and supplied with 150 ng/ml of nerve growth factor (NGF).

Explants and dissociated cultures were fixed for 15 min in 4% paraformaldehyde (PFA, Sigma-Aldrich, Seelze, Germany).

To analyze neurite outgrowth, samples were incubated overnight at 4° C. with anti-βIII tubulin (monoclonal mouse 1:1000; n. of catalogue: T8660, Sigma Aldrich) and Schwann cell specific α-S100 antibody (1:1000; n. of catalogue: HPA015768, Sigma) primary antibodies followed by 1 hr incubation at room temperature with secondary antibodies: anti-mouse IgG Alexa-Fluor-488 conjugated (n. of catalogue: A11029, Life Technologies) and goat α-rabbit Cy3 (n. of catalogue: 111-165-003, Li Starfish) respectively.

Surgical Procedures, Application of the Composition in Form of a Solid Film and Clinical Evaluation A primary outcome of the study was to evaluate the feasibility of intraoperative application of a chitosan film produced as disclosed above on neurovascular bundles at the end of a nerve-sparing robot-assisted radical prostatectomy (RARP).

Secondary outcomes were the following:

to assess the early recovery of sexual potency (at 1, 3 and 6 months) and the long term recovery (12 months) after nerve-sparing RARP with chitosan film (sexual potency recovery was defined as recovery of spontaneous erections or intercourses);

to perform a match-paired analysis with patients undergoing nerve sparing RARP without using of protective chitosan film applied on neurovascular bundles.

Study Population

Patients with an indication for nerve sparing RARP for prostate cancer were enrolled for the study at the Urology Department of San Luigi Gonzaga Hospital (Turin, Italy).

Inclusion Criteria

The inclusion criteria for patient admission to the study were the following:
age >18 years
informed consent for the study participation
histological diagnosis of prostate cancer
indication to nerve sparing RARP
preoperative IIEF5 Questionnaire >17
Exclusion Criteria
The exclusion criteria were the following:
contraindications to RARP
significant comorbidities (ie. smoking, diabetes mellitus, arterial hypertension)
age >72 years
Study Design Eligible patients in accordance with previous inclusion criteria have been submitted to the following process:
Evaluation of inclusion and exclusion criteria;
Nerve-sparing RARP and intraoperative application of chitosan film produced as disclosed above on the neurovascular bundles;
Uro-oncologic follow-up according to pathological results (visits at 1, 3, 6, 12 months after surgery);
Andrologic follow-up (visits at 1, 3, 6, 12 months after surgery).
Patient Sample Size (for the Match-Paired Analysis Only)
At least 83 patients (72+10-15% to compensate for the drop-out) were admitted to the study.
Statistics The sample size, as previously reported, is based on the match-paired analysis of patients undergoing nerve sparing RARP followed by the application of the chitosan composition on the neurovascular bundle vs. patients undergoing nerve sparing RARP without application of the chitosan composition on the neurovascular bundle.

The sample size was calculated on the basis of the differences between the two groups obtained from the analysis of the literature (Rabbani et al., Factors predicting recovery of erections after radical prostatectomy, J Urol 2000, 164, 1929; Ficarra et al., Systematic review and meta-analysis of studies reporting potency rates after robot-assisted radical prostatectomy, Eur Urol. 2012, 62, 418) which shows that the rate of sexual potency maintenance after nerve-sparing RARP amount to 50% while the expected rate after use of chitosan films is more than 70%.

To reject the null hypothesis of an equal sexual potency maintenance rate for both groups 83 patients have been enrolled in the group of patients undergone nerve-sparing RARP followed by the application of the chitosan composition in order to obtain a statistical power higher than 70% with an accepted error of 0.05.

Patients in the control group who underwent nerve sparing RARP without application of the chitosan composition has been retrospectively selected from the institutional database of the Urology Department.

All patients were continent and potent before RARP, as assessed by validated questionnaires:
IIEF-5, SEAR and EPIC questionnaires for potency as disclosed for example in Rosen et al., The international index of erectile function (IIEF): a multidimensional scale for assessment of erectile dysfunction, Urology 1997, 49, 822; Zymanski et al., Development and validation of an abbreviated version of the Expanded Prostate Cancer Index Composite Instrument for measuring health-related quality of life among prostate cancer survivors, Urology 2010, 76, 1245.

IPSS and IPSS-QoL for continence as disclosed in Sarasin et al., Can a urinary tract symptom score predict the development of postoperative urinary retention in patients undergoing lower limb arthroplasty under spinal anaesthesia? A prospective study. Ann R Coll Surg Engl 2007, 89, 192.

Nerve bundle preservation during RARP is vital for improved postoperative potency and continence.

Radical prostatectomy was performed by using the intrafascial dissection technique (nerve-sparing) uni- or bi-lateral.

Full nerve sparing dissection consists in a dissection following a plan on the prostate capsule that is medial or inner to the prostatic fascia on the anterolateral and posterolateral face of the prostate and anterior to the posterior prostatic fascia. The full nerve sparing dissection allows a complete conservation of the lateral prostatic fascia and then a maintenance of the neurovascular bundles.

Partial nerve sparing dissection (50% NS) consists in a dissection which preserves almost half of the lateral prostatic fascia. Intraoperatively, the right plane of dissection is identified by the presence of a fat strip over the prostate.

A chitosan film produced as disclosed above having a thickness of 30 µm, holes with a size of 160 µm, and a size of 3×4 cm was applied at the end of the reconstruction phase of the radical prostatectomy.

The film was immersed in a physiological solution to allow its insertion through a laparoscopic port and juxtaposed to the muscular wall where the neurovascular bundles are located.

Results

Proliferation Rate of Cancer Cells

Figure 4:
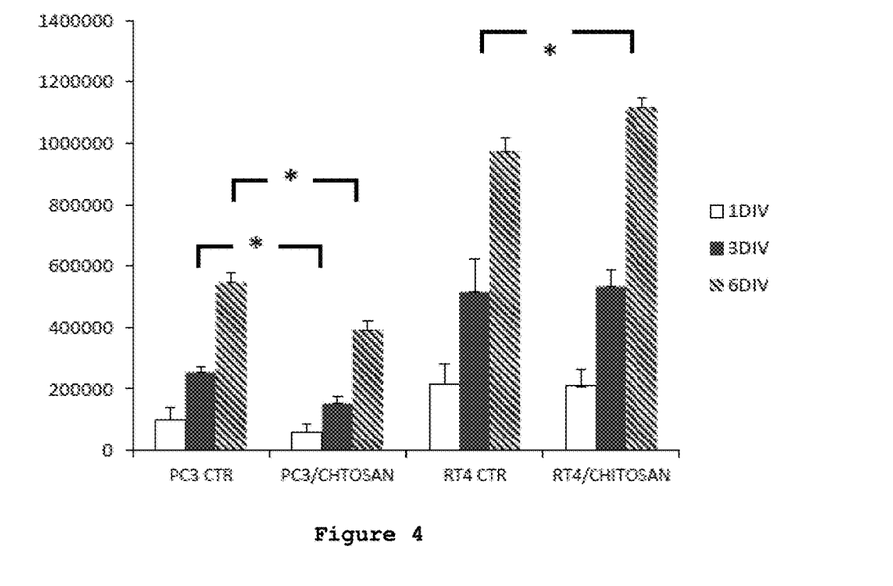
FIG. 4: Quantitative evaluation of PC3 cancer cells and RT4-D6P2T glial cells grown in a medium conditioned with dissolution products of a chitosan film (CTR=control)

FIG. 4 shows PC3 cancer cells grown in a medium conditioned with the dissolution products of chitosan films; the proliferation rate is lower, starting from the third day of culture, compared to the proliferation rate of the same cells cultured in a control medium. The difference is statistically significant ($p<0.05$).

These results thus demonstrate an antiproliferative activity of the dissolution products of chitosan films on the tumor cell line PC3.

The dissolution products of chitosan film do not cause the same effects on the population of glial cells, RT4-D6P2T; after six days culture it is possible to observe a significant increase in their proliferation rate, induced by the conditioned medium.

The absolutely innovative aspect of chitosan is represented by the two-fold effect on the tested cell populations, in which, on the one hand inhibits the proliferation of tumor cells and, on the other, promotes the growth of peripheral nervous glial cells, with a strong regenerative potential.

Nerve Regeneration

The evaluation of the neurons interaction with the chitosan composition herein disclosed represents a key preliminary step to establish, in vitro, the potential for neural regeneration.

Dissociated neuronal cultures of rat dorsal root ganglia (DRGs) (FIG. 5 panels A, B) and explants of vagus nerve ganglia (FIG. 5 panels C, D) are valuable models to evaluate the neuritic adaptation to different substrates.

Adults DRGs dissociated neurons and autonomic explants were cultured on chitosan films (FIG. 5, panels B, C, D) and on glass (FIG. 5, panel A), as positive control. After three days, a high neurite outgrowth was appreciated on both substrates. Careful observation led to detect a great sprouting and neurite extension on the chitosan films, which represents a permissive substrate for neurite regeneration, as demonstrated by the β-tubulin positive staining (white) and glial survival, S100 positive staining (gray).

Clinical Evaluation

The application of the composition comprising chitosan in form of a film on the neurovascular bundle of patients undergone RARP resulted in an increase of the potency recovery. At one month follow-up, potency was restored in 28.6% of patients with the bilateral full nerve sparing technique in the control group and in 41% of patients who underwent the bilateral full nerve sparing technique followed by the application of the chitosan composition in form of film (FIG. 6).

Figure 6:
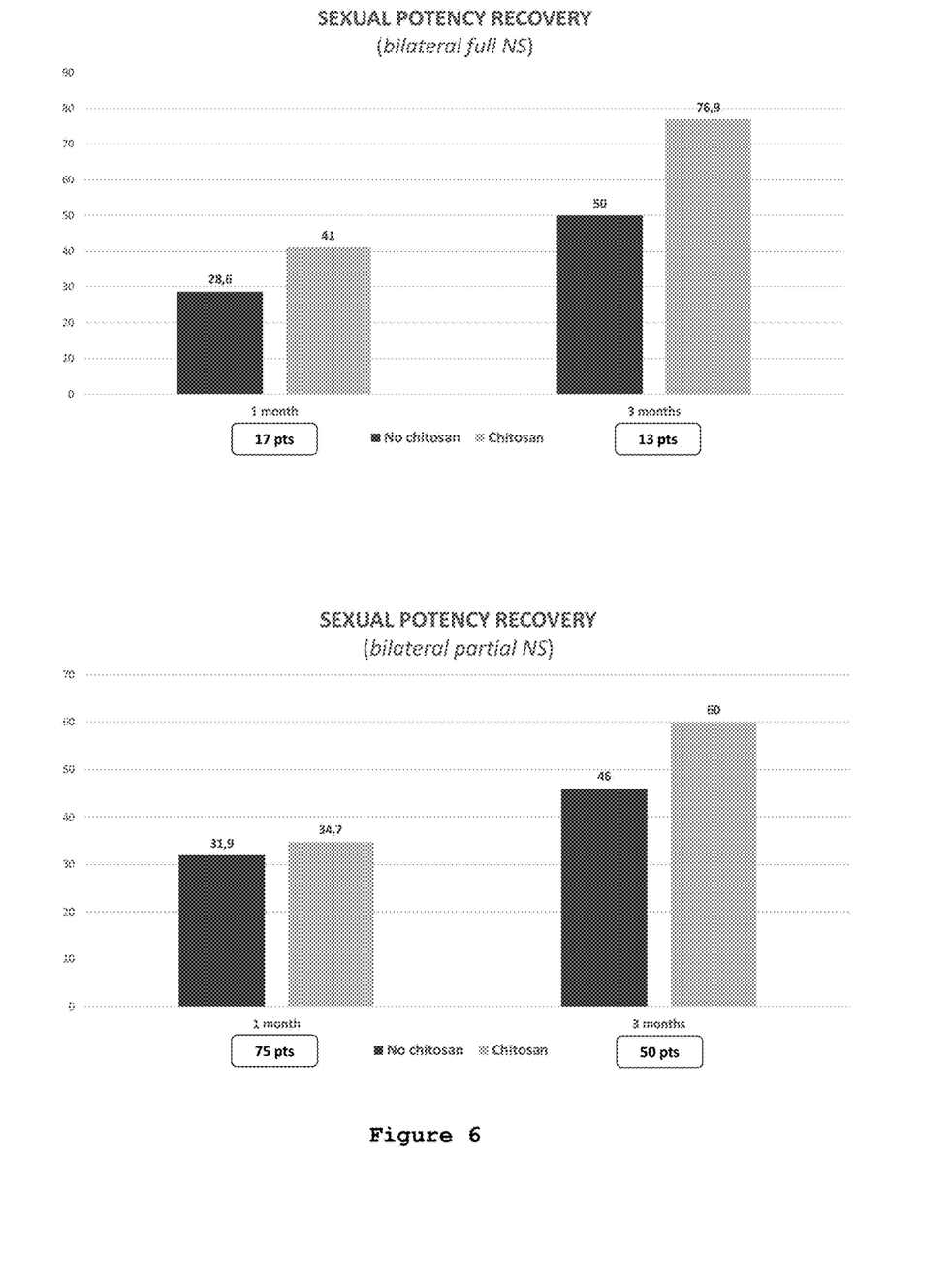
FIG. 6: Recovery of potency in patients undergone radical prostatectomy followed by application of a composition according to one embodiment of the instant disclosure.

The difference in terms of recovery is retained even three months after surgery; 76.9% of patients who underwent RARP and the application of the chitosan film recovered sexual potency vs. the 50% of patients of the control group (FIG. 6).

Similar results were obtained when comparing the two groups who underwent bilateral partial nerve sparing prostatectomy, with and without chitosan film application.

Moreover, it was possible to observe a reduced inflammation, infection and bleeding time, in the region of application, due to the biocompatibility, antimicrobial and haemostatic properties of chitosan films.

Therefore, the chitosan composition herein disclosed is able enhance the recovery of sexual potency without any adverse effects and without prolonging the operative time.

Of course, without prejudice to the underlying principle, the embodiments and the details of construction may vary, even significantly, with respect to what has been illustrated herein purely by way of non-limiting example, without thereby departing from the extent of protection. The above extent of protection is defined by the annexed claims.

The invention claimed is:

1. Method for treatment of incontinence and/or impotence in a subject undergoing prostatectomy, the method comprising applying a composition comprising chitosan to the prostatic neurovascular bundle of the subject undergoing prostatectomy.

2. Method according to claim 1, wherein the composition comprises chitosan in an amount of at least 50% by weight based on the non-aqueous components of the composition.

3. Method according to claim 1, wherein chitosan has a degree of acetylation of 40% or less.

4. Method according to claim 1, further comprising at least one bioactive constituent selected from the group consisting of proteins, peptides, nucleic acids, low molecular weight drugs and mixture thereof.

5. Method according to claim 1, wherein the composition is in form of a film.

6. Method according to claim 5, wherein the film has a thickness of 1000 μm or less.

7. Method according to claim 5, wherein the film contains at least one hole.

8. Method according to claim 7, wherein the at least one hole has a mean diameter size of 1000 μm or less.

\* \* \* \* \*

UNITED STATES PATENT AND TRADEMARK OFFICE
CERTIFICATE OF CORRECTION

PATENT NO. : 10,328,096 B2  
APPLICATION NO. : 15/641348  
DATED : June 25, 2019  
INVENTOR(S) : T. Freier, S. Geuna and F. Porpiglia Page 1 of 1

It is certified that error appears in the above-identified patent and that said Letters Patent is hereby corrected as shown below:

On the Title Page

Column 1, item (73) Assignees:
--Thomas Freier, Mainz (DE)--
Should read:
--"MONARCH BIOIMPLANTS GMBH S.R.L., ROOT D4, ("CH")--

Column 1, item (30) Foreign Application Priority Data:
Should read:
--"July 7, 2016 (IT) 102016000070911.--

Signed and Sealed this
Ninth Day of June, 2020

Andrei Iancu
*Director of the United States Patent and Trademark Office*